United States Patent [19]

Kane et al.

[11] 4,180,522
[45] Dec. 25, 1979

[54] N-(2-DIMETHYLAMINOALKYL)-3',4'-DICHLOROANILIDES

[75] Inventors: Michael P. Kane; Jacob Szmuszkovicz, both of Kalamazoo, Mich.

[73] Assignee: The Upjohn Company, Kalamazoo, Mich.

[21] Appl. No.: 934,239

[22] Filed: Aug. 16, 1978

Related U.S. Application Data

[63] Continuation of Ser. No. 838,767, Oct. 3, 1977, abandoned, which is a continuation of Ser. No. 746,863, Dec. 2, 1976, abandoned.

[51] Int. Cl.² ......................................... C07C 103/375
[52] U.S. Cl. ........................... 260/562 R; 260/557 R; 424/324
[58] Field of Search ................ 260/562 R, 562 P, 557

[56] References Cited

U.S. PATENT DOCUMENTS

| 2,944,081 | 7/1960 | Wright et al. | 260/562 P |
| 3,016,382 | 1/1962 | Wright et al. | 260/562 R |
| 3,234,276 | 2/1966 | Petracek | 260/558 P |
| 3,573,320 | 3/1971 | Jansen et al. | 260/305 |

OTHER PUBLICATIONS

Wagner et al., "Synthetic Organic Chemistry", John Wiley & Sons, N.Y., N.Y. 1953, pp. 665–668.

Primary Examiner—Arthur P. Demers
Attorney, Agent, or Firm—Hans L. Berneis; Robert A. Armitage

[57] ABSTRACT

The present specification provides compounds of the formula:

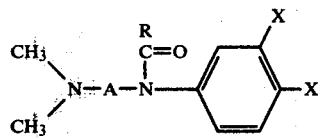

wherein A is a group selected from —(CH$_2$)$_2$—; —(CH$_2$)$_3$—; —(CH$_2$)$_4$—;

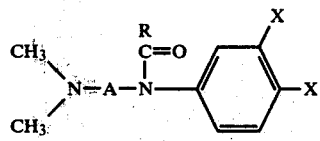

wherein R is ethyl, vinyl, or cyclopropyl; and wherein X is bromo or chloro. These compounds, including the pharmacologically acceptable salts thereof, are disclosed as useful antidepressant agents in warm-blooded animals, particularly man.

10 Claims, No Drawings

N-(2-DIMETHYLAMINOALKYL)-3',4'-DICHLOROANILIDES

This is a continuation of application Ser. No. 838,767, filed Oct. 3, 1977, now abandoned, which is a continuation of application Ser. No. 746,863, filed Dec. 2, 1976, now abandoned.

BACKGROUND OF THE INVENTION

Field of the Invention

This invention is concerned with new organic compounds and more specifically with dimethylaminoalkyl-3',4'-dihaloanilides III, pharmacologically acceptable acid addition salts, the use of compounds of formula III and its salts and a synthesis therefor.

The novel compounds III and the processes of production thereof can be illustratively represented as follows:

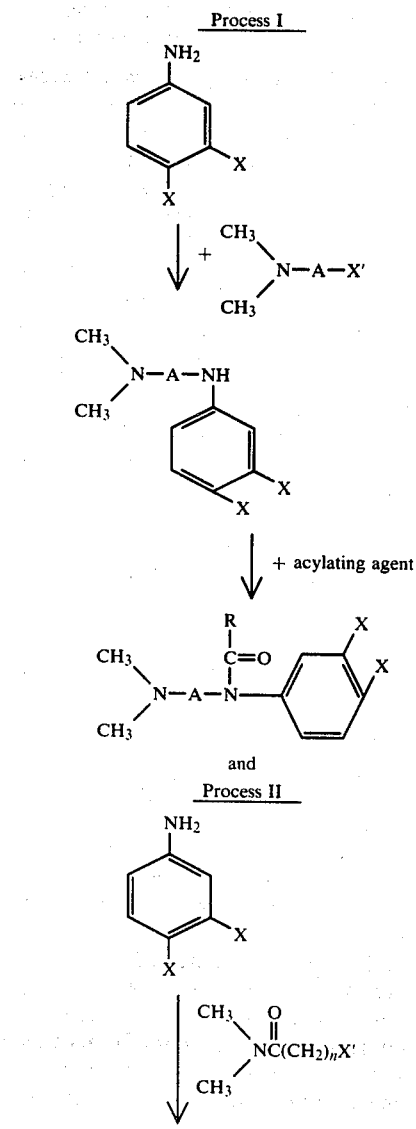

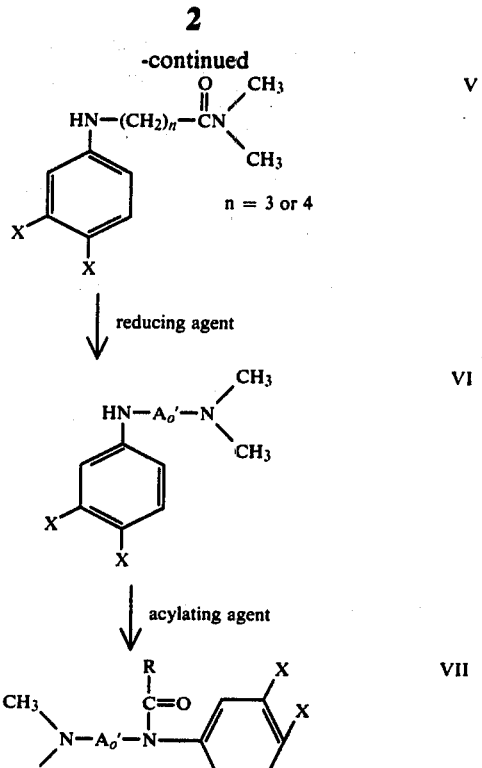

wherein $A_o$ is selected from the group consisting of —(CH$_2$)$_2$—; —(CH$_2$)$_3$—;

$$-CH_2-\overset{1}{C}H-;\text{ and }-\overset{1}{C}H-\overset{2}{C}H_2-;\ -CH_2-CH-CH_2-;$$
$$\phantom{-CH_2-}CH_3\phantom{H-;\text{ and }-}CH_3\phantom{CH_2-;\ -CH_2-}CH_3$$

wherein $A_o'$ is —(CH$_2$)$_4$ or —(CH$_2$)$_5$—; wherein X is bromo or chloro; wherein X' is chloro, bromo or iodo and wherein R is ethyl, cyclopropyl or vinyl.

The more preferred end products of this synthesis are of the formula IIIA:

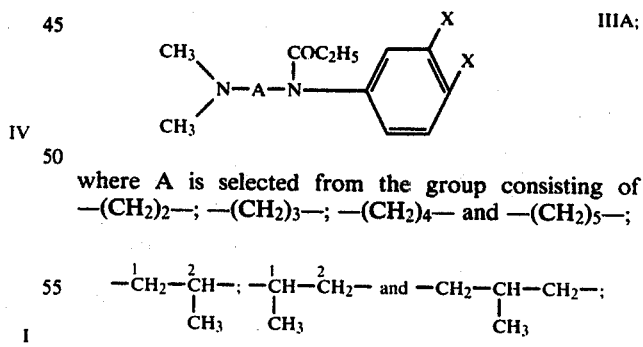

where A is selected from the group consisting of —(CH$_2$)$_2$—; —(CH$_2$)$_3$—; —(CH$_2$)$_4$— and —(CH$_2$)$_5$—;

$$-\overset{1}{C}H_2-\overset{2}{C}H-;\ -\overset{1}{C}H-\overset{2}{C}H_2-\text{ and }-CH_2-CH-CH_2-;$$
$$\phantom{-}CH_3\phantom{H-;\ -}CH_3\phantom{CH_2-\text{ and }-CH_2-}CH_3$$

and wherein X is bromo or chloro.

The most preferred compounds of this invention are of the formula IIIB:

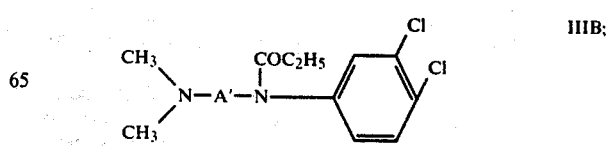

wherein A' is ethylene or trimethylene.

Compounds of similar structures are shown in U.S. Pat. No. 3,016,281; however, these patented compounds are analgesics. The present compounds on the other hand are anti-depressive.

U.S. Pat. No. 3,573,320 discloses but does not claim anti-depressant agents of the formula:

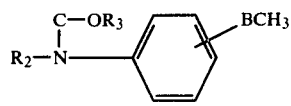

wherein B is oxygen or sulfur; R₂ is

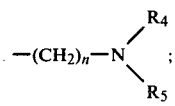

in which n is 2 or 3; R₄ is H or alkyl, or

is morpholino, piperidino, pyrrolidino or piperazino; R₃ is alkyl, aryl, etc.

U.S. Pat. No. 3,234,276 and French Pat. No. 2,073,286 (Chem. Abstracts 77,88108) also claim related products, but for different uses.

However, none of the references above reads on the new anti-depressant agents of this invention.

The process I of this invention comprises: heating a mole equivalent of 3,4-dihaloaniline I with about ½ to 1 mole equivalent of a dimethylaminoalkyl halide to give compound II, (the excess of compound I provides the base to accept the hydrogen halide moiety generated in this reaction) and acylating compound II, e.g., with the chlorides or bromides of propionic acid, acrylic acid or cyclopropanecarboxylic acid in the presence of a base, or with propionic anhydride to obtain the corresponding compound of Formula IV.

The process II of this invention comprises: heating a mole equivalent of 3,4-dihaloaniline with about 1 mole equivalent of N,N-dimethylamino halobutyramide or -valeramide to give compound V; reducing V with metal hydride to give compound VI; and acylating compound VI to give compound VII.

Such metal hydrides include: lithium aluminum hydride, sodium cyanoborohydride, borane, diborane.

The invention also encompasses the pharmacologically acceptable acid addition salts of the compounds of formula III (including the preferred compounds of formulae IIIA and IIIB). These salts comprise the hydrochlorides, hydrobromides, sulfates, malates, maleates, tartrates, lactates, citrates, cyclohexanesulfamates, methanesulfonates and the like which are prepared by reacting compounds of Formula III with a stoichiometrically calculated amount of the selected acid, in aqueous or ethereal solution, and finally evaporating the solvent.

The invention also comprises the use of the compounds of Formula III or the salts thereof, described above, in pharmaceutical formulations for treating depressions of endogenous and/or exogenous character.

PREFERRED EMBODIMENT OF THE INVENTION

The new compounds of Formula III were tested for anti-depressant activity by standard tests used in the art described below.

The main function of an anti-depressant is to return the depressed individual to normal function. This should be carefully differentiated from psychic stimulants such as the amphetamines which produce overstimulation in the normal individual.

Many different methods have been and are used to evaluate anti-depressant activity. In general these methods involve antagonism to a depressant such as reserpine or tetrabenazine or a synergistic increase of the toxicity of certain compounds (i.e., yohimbine or 3,4-dihydroxyphenylalanine) and comparison of the drug action of a new compound with other known antidepressants. No single test alone can determine whether or not a new compound is an anti-depressant, but the profile evidenced by various tests establishes that antidepressant action is present. A number of such tests are described below.

(A) Hypothermic Tests with Oxotremorine, 1-[4-(1-Pyrrolidinyl)-2-Butynyl]-2-Pyrrolidinone Oxotremorine (as well as apomorphine and tetrabenazine) produces hypothermic responses in mice. This response is blocked by anti-cholinergics and anti-depressants such as atropine and imipramine.

Oxotremorine produces a very pronounced hypothermia which reaches a peak 60 minutes after administration.

Method: The present compounds are injected intraperitoneally in 4 male Carworth Farm (CF₁) mice, and the mice are placed in plastic cages for 30 minutes. Thereafter 1 mg/kg oxotremorine hydrochloride is injected subcutaneously, and the mice are placed in a refrigerator at 19° C. A set of 4 mice injected merely with saline and 30 minutes later with oxotremorine are similarly cooled in a refrigerator. Thirty minutes after the oxotremorine administration the body temperature of the mice is determined rectally by a thermistor probe. An increase of 4° F. in body temperature of the treated mouse (oxotremorine and test compound) over the control mouse (oxotremorine treated only) is indicative of anti-depressive activity.

(B) Potentiation of Yohimbine Aggregation Toxicity

The LD₅₀ of yohimbine hydrochloride in mice is 45 mg/kg, i.p. Administration of 20 mg/kg of yohimbine hydrochloride is non-lethal. If an anti-depressand is administered prior to the yohimbine hydrochloride the lethality is increased.

Four male CF mice, 18–22 g., are injected with 20 mg/kg yohimbine hydrochloride in saline solution in a 30° C. chamber. After two hours the number of lethalities are determined. No, or only one, mouse will be dead at this level of yohimbine hydrochloride.

If an anti-depressant compound is injected 30 minutes prior to the administration of the yohimbine hydrochloride, the lethality is increased. If 3 out of 4 mice die at a certain dosage of a test compound, the test result is considered to be a positive indicator of the anti-depressant activity of the compound.

(C) Apomorphine Gnawing Procedure

A group of 4 mice (male, $CF_1$, 18–22 g.) are administered the test compound intraperitoneally 1 hour prior to the subcutaneous injection of apomorphine hydrochloride 10 mg/kg. The mice are then placed individually in plastic boxes and observed for stereotyped gnawing. If 3 or 4 of the mice display this behavior, the compound is declared active at that dose.

The compounds described in the subsequent examples were tested and found to have activities equal to or better than commercial anti-depressants such as imipramine hydrochloride.

The pharmaceutical forms of compounds of formula III and salts thereof contemplated by this invention include pharmaceutical compositions suited for oral, parenteral and rectal use e.g., tablets, powder packets, cachets, dragees, capsules, solutions, suspensions, sterile injectable forms, suppositories, bougies and the like. Suitable diluents or carriers, such as carbohydrates, lactose, sucrose, mannitol, proteins, lipids, calcium phosphate, cornstarch, stearic acid, methylcellulose and the like, may be used as carriers or for coating purposes. Water or oils, such as coconut oil, sesame oil, safflower oil, cottonseed oil and peanut oil, may be used for preparing solutions or suspensions of the active drug. Artificial sweetening agents, coloring and flavoring agents may be added.

As antidepressants the compounds of formula III, (including IIIA and IIIB) and their pharmacologically acceptable acid addition salts can be used in dosages of 0.01–2 mg/kg, depending on the specific compound used and the weight, age and condition of the patient. Preferably, a dosage of 0.05 to 1 mg/kg is used in oral or injectable preparations, as described above, to alleviate depression of patients.

In the treatment of human depression unit dosages containing 1.0 to 30 mg. can be given from 1 to 4 times daily, depending on body weight, age and conditions of the patient, as well as the particular compound of formula III employed. These unit dosages can be administered orally, or by injection subcutaneously, intravenously or intramuscular, or rectally.

The starting compounds for this invention are known 3,4-dihaloanilines, halo being chloro or bromo. Similarly, the reactants chloro- or bromo-dimethylaminoalkanes are well known in the art.

In carrying out the process of this invention the selected 3,4-dihaloaniline I is heated with a selected halo-1(N-dimethylamino)alkane, or an acid salt thereof in the presence of a base, with or without a solvent or suspending agent, to give compound III.

In the preferred embodiment of this invention, the 3,4-dihaloaniline is used in a ratio of 1 to 2 mole equivalents for each mole equivalent of the halodialkylaminoalkane as the free amine base or as base salt. If it is used as a salt, additional base is necessary to release the free base. When used in excess, the aniline I serves as that additional base; also, inorganic bases such as sodium or potassium bicarbonates or carbonates can be used as the additional base. Representative solvents, if such is used, are preferably those which reflux at more than 85° C. e.g., toluene, xylenes, trimethylbenzenes, ethylbenzene, dioxane, can be used as solvents or suspending agents. The reaction is preferably carried out between 100° C. and the boiling temperature of the solvent or suspending agent. The time of reaction under these conditions is between 1 and 5 days. After the reaction is terminated the product (II), a N,N-dimethyl-N'-(3,4-dihalophenyl)alkanediamine, is recovered by conventional means, such as extraction of the diamine II as the base with organic water-immiscible solvents, e.g., ether, benzene, toluene, or as the salt, for example, as the hydrochloride, in the acidified aqueous phase. The compound is purified by conventional means, e.g., additional extractions, chromatography and recrystallization. It is also obtainable as a salt, e.g., as the hydrochloride.

Compound II is acylated in the conventional manner, that is, by reacting compound II with the corresponding acyl halide, propionyl, acryloyl or cyclopropanecarbonyl chloride or bromide or anhydride, for example, propionic anhydride. If an acyl halide is used, a base such as triethylamine, methyldiethylamine, N-methylpiperidine or the like, is preferably used with it. The reaction is carried out with the acid halide and a base, or with acid anhydride and generally a solvent, e.g., methylene chloride, chloroform, tetrahydrofuran, dioxane, or the like. The reaction time is 1 to 8 hours at room temperature. When propionic anhydride is used, from 2 to 24 hours at 75°–100° C. (steam bath) is necessary. After the reaction is completed, the compound III is isolated as the free base or as its acid addition salt, by adding an acid to the mixture and extracting with water. The product is further purified by crystallization, additional extractions or chromatography. Compounds III or their acid addition salts in their crystalline state can be isolated as solvates, e.g., with a discreet quantity of solvent, e.g., water, ethanol and the like, associated physically, and thus removable without effective alteration of the chemical entity per se.

The following examples are illustrative of the product, processes and use of the present invention, but are not to be construed as limiting.

EXAMPLE 1

N,N-dimethyl-N'-(3,4-dichlorophenyl)ethylenediamine and its dihydrochloride

A solution of 3,4-dichloroaniline (71.7 g., 0.44 mole) and 1-chloro-2-dimethylaminoethane (23.8 g., 0.22 mole), (obtained from its hydrochloride acid addition salt by neutralization and distillation) is heated on a steam bath for 72 hours. The mixture is treated with 20% aqueous sodium hydroxide (200 ml.) and extracted with ether. The extract is washed with saturated sodium chloride solution, dried over anhydrous magnesium sulfate and evaporated. Distillation at reduced pressure gives 50.6 g. (b.p. 128°–135°/0.1 mm.) of a mixture of 3,4-dichloroaniline and of the product N,N-dimethyl-N'-(3,4-dichlorophenyl)ethylenediamine. The mixture is chromatographed on 500 g. silica gel eluting with chloroform in 1000 ml. factions. Fractions 1–11 contain 44.6 g. of 3,4-dichloroaniline. Further elution with 3000 ml. 20% methanol in $CHCl_3$ gives 4.4 g. of N,N-dimethyl-N'-(3,4-dichlorophenyl)ethylenediamine as an oil. The hydrochloride of N,N-dimethyl-N'-(3,4-dichlorophenyl)ethylenediamine is prepared by reaction with excess ethereal hydrogen chloride and is recrystallized from methanol-ether to give 4.2 g. (6.2%) of N,N-dimethyl-N'-(3,4-dichlorophenyl)ethylenediamine (melting point 151°–153° C.)

Anal. Calcd. for $C_{10}H_{14}Cl_2N_2.2\ HCl.2CH_3OH$: C, 39.25; H, 5.63; Cl, 44.03; N, 8.70. Found: C, 39.58; H, 5.51; Cl, 44.03; N, 9.06.

Heating the methanol solvate dihydrochloride in vacuo at 80° for 72 hours yields the pure unsolvated dihydrochloride.

The dihydrochloride is treated with aqueous sodium carbonate until about neutral, the mixture is then extracted twice with ether, and the ether evaporated to give the free base N,N-dimethyl-N'-(3,4-dichlorophenyl)ethylenediamine.

EXAMPLE 2

N-[2-(dimethylamino)ethyl]-3',4'-dichloropropionanilide and its maleate

Propionyl chloride (2.60 g., 0.028 mole) is added over a period of 30 minutes to a solution of triethylamine (2.84 g., 0.028 mole) and N,N-dimethyl-N'-(3,4-dichlorophenyl)ethylenediamine (3.26 g., 0.024 mole) in 100 ml. of methylene chloride. After 4 hours 100 ml. of aqueous saturated sodium bicarbonate is added. The organic layer is washed with saturated sodium chloride, dried over anhydrous magnesium sulfate and evaporated to a yellow oil. The maleic acid addition salt is prepared by reaction with maleic acid (1.62 g., 0.014 mole) in methanol-ether followed by recrystallization from ethanol-water.

Anal. Calcd. for $C_{13}H_{18}Cl_2N_2O.C_4H_4O_4$: C, 50.39; H, 5.47; Cl, 17.50; N, 6.91. Found: C, 50.15; H, 5.46; Cl, 17.56; N, 6.82.

Treating the maleate salt with aqueous sodium hydroxide, extracting the mixture with ether and evaporating the ether layer, gives the free base N-[(2-dimethylamino)ethyl]-3',4'-dichloropropionanilide.

Treating the free base with hydrogen chloride in ether gives the hydrochloride of N-[(2-dimethylamino)ethyl]-3',4'-dichloropropionanilide.

EXAMPLE 3

N,N-dimethyl-N'-(3,4-dichlorophenyl)trimethylene-1,3-diamine and its dihydrochloride A mixture of 3,4-dichloroaniline (60.8 g., 0.38 mole), 1-chloro-3-dimethylaminopropane hydrochloride (39.5 g., 0.25 mole), and sodium carbonate (53.0 g., 0.50 mole) in toluene (250 ml.) is refluxed for 72 hours. Water is added; the organic layer is washed with water and extracted with 10% hydrochloric acid. The acidic phase is washed with ether, made basic with 40% sodium hydroxide and extracted with ether. The ether is washed with saturated sodium chloride solution, dried over anhydrous magnesium sulfate and evaporated. The crude oil is chromatographed on 100 g. silica gel in a sintered glass funnel eluting three times with 250 ml. chloroform followed with 700 ml. methanol. Evaporation of the methanol gives 5.1 g. of N,N-dimethyl-N'-(3,4-dichlorophenyl)trimethylene-1,3-diamine as a brown oil. The hydrochloride is prepared by treatment with excess ethereal hydrogen chloride and recrystallization from methanol-ether to give 5.1 g. of N,N-dimethyl-N'-(3,4-dichlorophenyl)trimethylene-1,3-diamine dihydrochloride of melting point 182°–183° C.

Anal. Calcd. for $C_{11}H_{18}Cl_2N_2.2HCl$: C, 41.27; H, 5.67; Cl, 44.31; N, 8.75. Found: C, 41.63; H, 5.74; Cl, 43.92; N, 8.73.

EXAMPLE 4

N-[3-(dimethylamino)propyl]-3',4'-dichloropropionanilide and its hydrochloride

A solution of N,N-dimethyl-N'-(3,4-dichlorophenyl)-trimethylene-1,3-diamine (3.70 g., 0.015 mole) and propionic anhydride (20 ml.) is heated on a steam bath overnight. Water (100 ml.) is added and heating continued for 30 minutes. The mixture is cooled, made basic with 20% aqueous sodium hydroxide and extracted with ether. The ether layer is washed with saturated sodium chloride solution, dried over anhydrous magnesium sulfate and evaporated to a yellow oil. The hydrochloride is prepared by treatment with excess ethereal hydrogen chloride followed by recrystallization from methanol-ether to give 3.3 g. of N-[(3-dimethylamino)propyl]-3'4'-dichloropropionanilide hydrochloride.

Anal. Calcd. for $C_{14}H_{20}Cl_2N_2O.HCl$: C, 49.50; H, 6.23; Cl, 31.31; N, 8.25. Found: C, 49.59; H, 6.31; Cl, 31.61; N, 8.52.

Treatment of this hydrochloride with aqueous sodium hydroxide, extraction with ether and evaporation of the ether gives the free base N-[(3-dimethylamino)propyl]-3',4'-dichloropropionanilide.

EXAMPLE 5

N'-(3,4-dichlorophenyl)-N,N,1-trimethylethylenediamine and N'-(3,4-dichlorophenyl)-N,N,2-trimethylethylenediamine A mixture of 16.2 g. of 3,4-dichloroaniline, 39.6 g. (0.25 mole) of 2-chloro-1-dimethylaminopropane hydrochloride, 26.5 g. (0.25 mole) of sodium carbonate and 21.1 g. (0.25 mole) of sodium bicarbonate in 200 ml. of toluene are heated for 72 hours on a steam bath. Then 250 ml. of water is added, the organic phase is separated and then evaporated in vacuo to give 17 g. of a mixture of N',(3,4-dichlorophenyl)-N,N,1-trimethyl ethylenediamine and N'-(3,4-dichlorophenyl)-N,N,2-trimethylethylenediamine, which also contained some unreacted starting material.

EXAMPLE 6

N-[(2-dimethylamino-1-methyl)ethyl]-3',4'-dichloropropionanilide and its hydrochloride The mixture obtained in Example 5 and 50 ml. of propionic anhydride are heated for 18 hours on a steam bath. Thereafter 400 ml. of water is added and heating continued for one hour. The mixture is then made basic with aqueous 40% sodium hydroxide solution, extracted with 500 ml. of ether, the extracts washed with 200 ml. of water and then extracted again with 200 ml. of aqueous 10% hydrochloric acid solution. This (second) extract is washed with 250 ml. of ether, made basic with aqueous 40% sodium hydroxide solution, extracted with ether and the ether extracts washed with 100 ml. of saturated sodium chloride solution. The extracts are then dried over anhydrous magnesium sulfate and evaporated. The remaining oily material is chromatographed over 500 g. of silica gel, eluting with ethyl acetate. Two hundred fractions of 20 ml. each are obtained, of which fractions 91 to 180 contain a single component. Fractions 91 to 180 after evaporation give 6.5 g. of a yellow oil. This oil is the free base, N-[(2-dimethylamino-1-methyl)ethyl]-3',4'-dichloroanilide.

The oil is treated with excess ethereal hydrogen chloride, and the thus precipitated salt twice recrystallized from methanol-ether (1/10-V/V) to give 5.6 g. (16%) of N-[(2-dimethylamino-1-methyl)ethyl]-3',4'-dichloropropionanilide hydrochloride of melting point 196° to 197° C.

Anal. Calcd. for $C_{14}H_{10}N_2Cl_2O.HCl-H_2O$: C, 47.10; H, 5.87; N, 7.84. Found: C, 47.45; H, 5.99; N, 7.91.

EXAMPLE 7

N-[(2-dimethylamino-2-methyl)ethyl]-3',4'-dichloropropionanilide

After completion of elution of the free base in Example 6 the chromatographic column is further eluted with ethyl acetate: methanol (9:1). Fractions of 500 ml. each are taken. Fractions 5 through 8 are combined and evaporated to give 2.2 g. of a yellow oil which is N-[(2-dimethylamino-2-methyl)ethyl]-3',4'-dichloropropionanilide. This product is treated with 1 g. of oxalic acid in 20 ml. of methanol and 200 ml. of ether. It is then recrystallized from methanol-ether to give 2.3 g. (6%) of N-[(2-dimethylamino-2-methyl)ethyl]-3',4'-dichloropropionanilide oxalate of melting point 183° C.

Anal. Calcd. for $C_{14}H_{20}N_2Cl_2O \cdot C_2H_2O_4$: C, 48.86; H, 5.64; N, 7.12; Cl, 18.03. Found: C, 49.04; H, 5.63; N, 7.31; Cl, 18.30.

The oxalate is treated with aqueous sodium hydroxide, the aqueous mixture extracted with ether and the ether solution treated with gaseous hydrogen chloride to give the hydrochloride salt of N-[(2-dimethylamino-2-methyl)ethyl]-3',4'-dichloropropionanilide.

EXAMPLE 8

N-[(3-dimethylamino-2-methyl)propyl]-3',4'-dichloropropionanilide

(A)

N'-(3,4-dichlorophenyl)-N,N,2-trimethylpropane-1,3-diamine

Forty-three grams (0.75 mole) of 1-chloro-2-methyl-3-(dimethylamino)propane hydrochloride is heated with 25 ml. of 40% aqueous sodium hydroxide in 250 ml. of ether. To this mixture is added 16 g. (0.10 mole) of 3,4-dichloroaniline. The ether is removed by distillation and the mixture is heated on the steam bath for 72 hours. Thereafter the mixture is treated with 200 ml. of 20% aqueous sodium hydroxide, treated for 1 hour on the steam bath and extracted with 250 ml. of ether. The extracts are dried over anhydrous magnesium sulfate and evaporated to give an oil. The black oil is suction-filtered through 200 g. of silica eluting with methylene chloride until no more material elutes. The filtrate is evaporated to give N-(3,4-dichlorophenyl)-N,N,2-trimethylpropane-1,3-diamine as an orange oil.

(B)

N-[(3-dimethylamino-2-methyl)propyl]-3',4'dichloropropionanilide

The orange-colored oil of Example 8A is treated with 25 ml. of propionic anhydride and heated on a steam bath for 20 hours. Thereafter 100 ml. of water is added to the reaction mixture. The mixture is then basified with aqueous 40% sodium hydroxide, extracted with 250 ml. of ether, the extracts washed with saturated sodium chloride solution, dried over anhydrous magnesium sulfate and evaporated to give the base N-[(3-dimethylamino-2-methyl)propyl]-3',4'-dichloropropionanilide. The free base is converted to its hydrochloride salt with excess of etheral hydrogen chloride. The compound is recrystallized from methanol-ether (1/12 V/V) to give 2.8 g. (8%) of N-[(3-dimethylamino-2-methyl)propyl]-3',4'-dichloropropionanilide hydrochloride of melting point 209° to 210° C.

Anal. Calcd. for $C_{15}H_{22}N_2Cl_2O \cdot HCl$: C, 50.93; H, 6.55; N, 7.92; Cl, 30.07. Found: C, 51.16; H, 6.51; N, 8.10; Cl, 30.07.

EXAMPLE 9

N-[(2-dimethylamino)ethyl]-3',4'-dibromopropionanilide

In the manner given in Example 1, a mixture of 3,4-dibromoaniline and 1-chloro-2-dimethylaminoethane is heated for 72 hours at 90° to 100° C. to give N,N-dimethyl-N-(3,4-dibromophenyl)ethylenediamine.

In the manner given in Example 2, to a solution of N,N-dimethyl-N'-(3,4-dibromophenyl)ethylenediamine and triethylamine is added propionyl chloride to give N-[2-(dimethylamino)ethyl]-3',4'-dibromopropionanilide.

EXAMPLE 10

N-[3-(dimethylamino)propyl]-3',4'-dibromopropionanilide

In the manner given in Example 1, a mixture of 3,4-dibromoaniline and 1-chloro-3-dimethylaminopropane is heated for 72 hours at 90° to 100° C. to give N,N-dimethyl-N'-(3,4-dibromophenyl)trimethylene-1,3-diamine.

In the manner given in Example 2, to a solution of N,N-dimethyl-N'-(3,4-dibromophenyl)trimethylene-1,3-diamine and triethylamine is added propionyl chloride to give N-[3-(dimethylamino)propyl]-3',4'-dibromopropionanilide.

EXAMPLE 11

N-[3-(dimethylamino)propyl]-3',4'-dibromocyclopropanecarboxanilide

In the manner given in Example 1, 3,4-dibromoaniline, 1-chloro-3-dimethylaminopropane hydrochloride, sodium carbonate and sodium bicarbonate are heated in toluene to give N,N-dimethyl-(3,4-dibromophenyl)-trimethylenediamine.

Heating the diamine with cyclopropanecarbonyl chloride in the presence of triethylamine, similarly to Example 2, provides the corresponding N-[3-(dimethylamino)propyl]-3',4'-dibromocyclopropanecarboxanilide.

Treating this anilide with hydrogen chloride in ether provides the corresponding N-[3-(dimethylaminopropyl)]-3',4'-dibromocyclopropanecarboxanilide hydrochloride.

EXAMPLE 12

N-[2-(dimethylamino)ethyl]-3',4'-dichloroacrylanilide

In the manner given in Example 1, 3,4-dichloroaniline, 1-chloro-2-dimethylaminoethane hydrochloride, and sodium bicarbonate are heated to give N,N-dimethyl-N'-(3,4-dichlorophenyl)ethylenediamine.

Heating the diamine with acryloyl chloride in the presence of triethylamine, similarly to Example 2, provides the corresponding N-[2-(dimethylamino)ethyl]-3',4'-dichloroacrylanilide.

Treating this anilide with hydrogen chloride in ether provides the corresponding N-[2-(dimethylaminoethyl]-3',4'-dichloroacrylanilide hydrochloride.

EXAMPLE 13

N-[(3-dimethylamino-2-methyl]propyl]-3',4'-dibromopropionanilide

In the manner given in Example 8A, 3,4-dibromoaniline, 1-chloro-2-methyl-3-dimethylaminopropane hydrochloride and sodium hydroxide are heated to give N'-(3,4-dibromophenyl)-N,N,2-trimethylpropylene-1,3-diamine.

Heating the diamine with propionyl chloride in the presence of triethylamine, similarly to Example 2, provides the corresponding N-[(3-dimethylamino-2-methylpropyl]-3',4'-dibromopropionanilide.

Treating this anilide with hydrogen chloride in ether provides the corresponding N-[3-(dimethylamino-2-methyl)propyl]-3',4,-dibromopropionanilide hydrochloride.

EXAMPLE 14

N-[(3-dimethylamino-2-methyl)propyl]3',4'-dibromocyclopropanecarboxanilide

In the manner given in Example 5, 3,4-dibromoaniline, 3-chloro-2-methyl-1-dimethylaminopropane hydrochloride and sodium carbonate are heated in toluene to give N'-(3,4-dibromophenyl)-N,N,2-trimethylpropane-1,3-diamine.

Heating the diamine with cyclopropanecarbonyl chloride in the presence of triethylamine similarly to Example 2, provides the corresponding N-[(3-dimethylamino-2-methyl)propyl]-3',4'-dibromocyclopropanecarboxanilide.

Treating this anilide with hydrogen chloride in ether provides the corresponding N-[(3-dimethylamino-2-methyl)propyl]-3',4'-dibromocyclopropanecarboxanilide hydrochloride.

EXAMPLE 15

N-[(3-dimethylamino-2-methyl)propyl]-3',4'-dibromoacrylanilide

In the manner given in Example 5, 3,4-dibromoaniline, 1-chloro-2-methyl-3-dimethylaminopropane hydrochloride, sodium carbonate and sodium bicarbonate are heated in toluene to give N-(3,4-dibromophenyl)-N,N,2-trimethylpropane-1,3-diamine.

Heating the diamine with acryloyl chloride in the presence of triethylamine, similarly to Example 2, provides the corresponding N-[(3-dimethylamino-2-methyl)-propyl]-3',4'-dibromoacrylanilide.

Treating this anilide with hydrogen chloride in ether provides the corresponding N-[(3-dimethylamino-2-methyl)propyl]-3',4'-dibromoacrylanilide hydrochloride.

EXAMPLE 16

N-[2-(dimethylamino)ethyl]-3',4'-dichlorocyclopropanecarboxanilide

In the manner given in Example 5, 3,4-dichloroaniline, 1-chloro-2-dimethylaminoethane hydrochloride and sodium carbonate are heated in toluene to give N,N-dimethyl-N'-(3,4-dichlorophenyl)ethylenediamine.

Heating the diamine with cyclopropanecarbonyl chloride in the presence of triethylamine, similarly to Example 2, provides the corresponding N-[(2-dimethylamino)ethyl]-3',4'-dichlorocyclopropane carboxanilide.

Treating this anilide with hydrogen chloride in ether provides the corresponding N-[(2-dimethylamino)ethyl]-3',4'-dichlorocyclopropanecarboxanilide hydrochloride.

EXAMPLE 17

N-[3-(dimethylamino)propyl]-3',4'-dichloroacrylanilide

In the manner given in Example 3, 3,4-dichloroaniline, 1-chloro-3-dimethylaminopropane hydrochloride and sodium carbonate are heated in toluene to give N,N-dimethyl-N'-(3,4-dichlorophenyl)propylene-1,3-diamine.

Heating the diamine with acryloyl chloride in the presence of triethylamine, similarly to Example 2, provides the corresponding N-[(3-dimethylamino)propyl]-3',4'-dichloroacrylanilide.

Treating this anilide with hydrogen chloride in ether provides the corresponding N-[(3-dimethylamino)-propyl]-3',4'-dichloroacrylanilide hydrochloride.

EXAMPLE 18

N'-(3,4-dibromophenyl)-N,N,1-trimethylethylenediamine and
N'-(3,4-dibromophenyl)-N,N,2-trimethylethylenediamine.

In the manner given in Example 5, a mixture of 3,4-dibromoaniline, 2-chloro-1-dimethylaminopropane hydrochloride, sodium carbonate and sodium bicarbonate is heated in toluene for 72 hours on a steam bath. After adding water to the mixture the organic phase is separated and evaporated to give a mixture of N-(3,4-dibromophenyl)-N,N,1-trimethylethylenediamine and N-(3,4-dibromophenyl)-N,N,2-trimethylethylenediamine.

EXAMPLE 19

N-[(2-dimethylamino-1-methyl)ethyl]-3',4'-dichloroacrylanilide, and its hydrochloride, and
N-[(2-dimethylamino-2-methyl)ethyl]-3',4'-dichloroacrylanilide and its hydrochloride In a manner similar to Example 6, the mixture of compounds obtained in Example 5 is treated with acryloyl chloride in the presence of triethylamine, then water added, basified with sodium hydroxide and extracted with ether. The ether extracts are washed with water and extracted with 10% hydrochloric acid. The hydrochloric acid extracts are washed with ether, the ether discarded, the aqueous solution made basic with sodium hydroxide and extracted with ether. The ether solution after washing is evaporated and chromatographed on silica gel with ethyl acetate to give N-[(2-dimethylamino-1-methyl)ethyl]-3',4'-dichloroacrylanilide.

Treatment of this compound with ethereal hydrogen chloride, gives N-[(2-dimethylamino-1-methyl)ethyl]-3,4-dichloroacrylanilide.

The silica gel column is further extracted with ethyl acetate:methanol to give N-[(2-dimethylamino-2-methyl) ethyl]-3',4'-dichloroacrylanilide, which is converted to its hydrochloride with an etheral solution of hydrogen chloride.

EXAMPLE 20

N-[(2-dimethylamino-1-methyl)ethyl]-3',4'-dichlorocyclopropanecarboxanilide, its hydrochloride and N-[(2-dimethylamino-2-methyl)ethyl]-3',4'-dichlorocyclopropanecarboxanilide and its hydrochloride In the manner given in Example 6, the mixture of compounds obtained in Example 5 is treated with cyclopropanecarbonyl chloride and triethylamine then water added, the mixture is basified with sodium hydroxide and extracted with ether. The ether extracts are washed with water and extracted with 10% hydrochloric acid. The hydrochloric acid extracts are washed with ether, the ether discarded, the aqueous solution made basic with sodium hydroxide and extracted with ether. The ether solution after washing is evaporated and chromatographed on silica gel with ethyl acetate to give N-[(2-dimethylamino-1-methyl)ethyl]-3',4'-dichlorocyclopropanecarboxanilide.

Treatment of this compound with ethereal hydrogen chloride, gives N-[(2-dimethylamino-1-methyl)ethyl]-3',4'-dichlorocyclopropanecarboxanilide.

The silica gel column is extracted further with ethyl acetate:methanol to give N-[(2-dimethylamino-2-methyl)ethyl]-3',4'-dichlorocyclopropanecarboxanilide, which is converted to its hydrochloride with an ethereal solution of hydrogen chloride.

EXAMPLE 21

N-[(2-dimethylamino-1-methyl)ethyl]-3',4'-dibromopropionanilide and its hydrochloride; and N-[(2-dimethylamino-2-methyl)ethyl]-3',4'-dibromopropionanilide and its hydrochloride In the manner given in Example 6, the mixture of compounds obtained in Example 18 is treated with propionic anhydride, then water added, basified with sodium hydroxide and extracted with ether. The ether extracts are washed with water and extracted with 10% hydrochloric acid. The hydrochloric acid extracts are washed with ether, the ether discarded, the aqueous solution made basic with sodium hydroxide and extracted with ether. The ether solution after washing is evaporated and chromatographed on silica gel with ethyl acetate to give N-[(2-dimethylamino-1-methyl)ethyl]-3',4'-dibromopropionanilide.

Treatment of this compound with ethereal hydrogen chloride, gives N-[(2-dimethylamino-1-methyl)ethyl]-3',4'-dibromopropionanilide hydrochloride.

The silica gel column is then extracted with ethyl acetate:methanol to give N-[(2-dimethylamino-2-methyl)ethyl]-3',4'-dibromopropionanilide, which is converted to its hydrochloride with an ethereal solution of hydrogen chloride.

EXAMPLE 22

N-[(2-dimethylamino-1-methyl)ethyl]-3',4'-dibromoacrylanilide and its hydrochloride; and N-[(2-dimethylamino-2-methyl)ethyl]-3',4'-dibromoacrylanilide and its hydrochloride In the manner given in Example 6, the mixture of compounds obtained in Example 18 is treated with acryloyl chloride and triethylamine, then water is added, the mixture is basified with sodium hydroxide and extracted with ether. The ether extracts are washed with water and extracted with 10% hydrochloric acid. The hydrochloric acid extracts are then washed with ether, the ether discarded, the aqueous solution made basic with sodium hydroxide and extracted with ether. The ether solution after washing is evaporated and chromatographed on silica gel with ethyl acetate to give N-[(2-dimethylamino-1-methyl]-ethyl]-3',4'-dibromoacrylanilide.

Treatment of this compound with ethereal hydrogen chloride gives N-[(2-dimethylamino-1-methyl)ethyl]-3',4'-dibromoacrylanilide hydrochloride.

The silica gel column is extracted further with ethyl acetate:methanol to give N-[(2-dimethylamino-2-methyl)ethyl]-3',4'-dibromoacrylanilide which is converted to its hydrochloride with an ethereal solution of hydrogen chloride.

EXAMPLE 23

N-[(2-dimethylamino-1-methyl)ethyl]-3',4'-dibromocyclopropanecarboxanilide and its hydrochloride; and N-[(2-dimethylamino-2-methyl)ethyl]-3',4'-dibromocyclopropanecarboxanilide and its hydrochloride In the manner given in Example 6, the mixture of compounds obtained in Example 18 is treated with cyclopropanecarbonyl chloride and triethylamine, then water is added, the mixture is basified with sodium hydroxide and extracted with ether. The ether extracts are washed with water and extracted with 10% hydrochloric acid. The hydrochloric acid extracts are washed with ether, the ether discarded, the aqueous solution made basic with sodium hydroxide and extracted with ether. The ether solution after washing is evaporated and chromatographed on silica gel with ethyl acetate to give N-[(2-dimethylamino-1-methyl)ethyl]-3',4'-dibromocyclopropanecarboxanilide.

Treatment of this compound with ethereal hydrogen chloride gives N-[(2-dimethylamino-1-methyl)ethyl]-3,4-dibromocyclopropanecarboxanilide hydrochloride.

The silica gel column is extracted further with ethyl acetate:methanol to give N-[(2-dimethylamino-2-methyl)ethyl]-3',4'dibromocyclopropanecarboxanilide, which is converted to its hydrochloride with an ethereal solution of hydrogen chloride.

EXAMPLE 24

N-(3',4'-dichlorophenyl)-N-[5-(dimethylamino)pentyl]-propionamide and its hydrochloride A solution of 57.6 g. (1.28 mole) of dimethylamine in 500 ml. of ether is cooled in an ice bath. Thereto is added dropwise over 30 minutes 50.0 g. (0.32 mole) of 5-chlorovaleryl chloride in 50 ml. of ether and then slowly 100 ml. of water. The organic layer is separated, washed with 100 ml. of aqueous saturated sodium bicarbonate solution, then dried over anhydrous magnesium sulfate and evaporated to give 41.5 g. (79%) of 5-chlorovaleryl N,N-dimethylamide as a yellow oil.

This oil is combined with a suspension of 3,4-dichloroaniline 40.5 g. (0.25 mole) and 1.0 g. of potassium iodide in 250 ml. of dimethylformamide and heated for 16 hours to reflux. The mixture is then poured into 1500 ml. of water and 100 ml. of aqueous 20% sodium hydroxide (pH of the 1600 ml. about 8). The precipitate which forms is collected by filtration, washed with water and recrystallized twice from ether to give 16.7 g. (23%) of 5-(3',4'-dichloroanilino)-N,N-dimethylvaleramide of melting point 114° C.

Analysis: $C_{13}H_{18}N_2Cl_2O$: Calculated: C, 53.99; H, 6.27; N, 9.69; Cl, 24.52. Found: C, 53.65; H, 6.28; N, 9.45; Cl, 24.41.

To a solution of 14.5 g. (0.05 mole) of 5-(3',4'-dichloroanilino)-N,N-dimethylvaleramide in 200 ml. of tetrahydrofuran cooled to −5° C. is added 200 ml. of borane (0.20 mole) solution in 200 ml. of tetrahydrofurane. The mixture is kept at room temperature overnight, then refluxed for 2½ hours on a steam bath to give a milky suspension. To this suspension is slowly added 100 ml. of 6 N aqueous hydrochloric acid. After about 30 minutes, effervescence (nitrogen gas) stops. The mixture is then distilled to remove the tetrahydrofuran, the remaining aqueous solution is washed with 200 ml. ether, then basified with 100 ml. of 40% aqueous sodium hydroxide and extracted with 300 ml. of ether. The ether extracts are washed with saturated aqueous sodium chloride solution then dried over anhydrous magnesium sulfate and evaporated to give 12.9 g. (94%) yield of N-(3',4'-dichlorophenyl)-N',N'-dimethyl-1,5-pentanediamine as a yellow oil.

Conversion of 1 g. of this oil to the dihydrochloride with hydrogen chloride in ether gives 0.8 g. (63%) yield of N-(3',4'-dichlorophenyl)-N',N'-dimethyl-1,5-pentanediamine dihydrochloride which melts at 183° C. (with decomposition).

Analysis: $C_{13}H_{20}N_2Cl_2 2HCl$: Calculated: C, 44.84; H, 6.37; N, 8.05; Cl, 40.74. Found: C, 44.96; H, 6.27; N, 8.04; Cl, 41.22.

The oily N-(3,4-dichlorophenyl)-N',N'-dimethyl-1,5-pentanediamine (11.9 g., 0.043 mole) and 80 ml. of propionic anhydride are heated on the steam bath overnight. To this mixture 250 ml. of water is added and heating is continued for 30 minutes. The mixture is basified with 150 ml. aqueous 40% sodium hydroxide and extracted with 200 ml. of ether. The ether extracts are washed with 100 ml. of aqueous saturated sodium chloride, dried over anhydrous magnesium sulfate and evaporated to give N-(3',4'-dichlorophenyl)-N-(5-dimethylaminopentyl)propionamide as a yellow oil.

The oxalate of N-(3',4'-dichlorophenyl)-N-(5-dimethylaminopentyl)propionamide is prepared with oxalic acid in 50 ml. of methanol:50 ml. of ether. This oxalate has a melting point of 166°–167° C.

Analysis for: $C_{16}H_{24}Cl_2N_2O \cdot C_2H_2O_4$: Calculated: C, 51.31; H, 6.22; N, 6.65; Cl, 16.83. Found: C, 51.74; H, 6.24; N, 6.64; Cl, 17.14.

As in Example 7, the oxalate salt is converted to the hydrochloride salt.

EXAMPLE 25

N-(3',4'-dichlorophenyl)-N-(4-dimethylaminobutyl)-propionamide and its hydrochloride A solution of 30 g. (0.2 mole) of N,N-dimethyl-4-chlorobutyramide [J. Falbe et al., Chem. Ber. 97 2544 (1964)], 32.4 g. (0.2 mole) of 3,4-dichloroaniline and 1 g. of potassium iodide in 250 ml. of dimethylformamide is refluxed for 17 hours. The reaction mixture is basified with 100 ml. of 20% aqueous sodium hydroxide in 1500 ml. of water. A precipitate is collected by filtration, washed with 500 ml. of ether and then dissolved in 500 ml. of methanol. After concentration to 200 ml., 13.5 g. of solid is obtained, which is 4-(3',4'-dichloroanilino)-N,N-dimethylbutyramide of melting point 154°–155° C.

Analysis: $C_{12}H_{16}Cl_2N_2O$: Calculated: C, 52.37; H, 5.86; N, 10.18; Cl, 25.77. Found: C, 52.73; H, 5.99; N, 10.04; Cl, 25.40.

In the manner given in Example 24, 4-(3',4'-dichloroanilino)-N,N-dimethylbutyramide is reduced with borane in tetrahydrofuarn to give N-(3',4'-dichlorophenyl)-N',N'-dimethylbutane-1,4-diamine as an oil.

The hydrochloride of this oil, made with hydrogen chloride gas in ether, has a melting point of 200°–201° C.

Analysis: $C_{12}H_{18}N_2Cl_2 2HCl$ (334.14): Calculated: C, 43.13; H, 6.03; N, 8.39; Cl, 42.45. Found: C, 43.62; H, 6.15; N, 8.91; Cl, 42.07.

N-(3',4'-dichlorophenyl)-N'N'-dimethylbutane-1,4-diamine (9.0 g.) is heated with 60 ml. of propionic anhydride to give N-(3',4'-dichlorophenyl)-N-(4-dimethylaminobutyl)propionamide as an oil.

This oil is treated with hydrogen chloride in ether to give 7.3 g. (63%) N-(3',4'-dichlorophenyl)-N-(4-dimethylamino)butyl propionamide hydrochloride, of melting point 162°–163° C.

Analysis: $C_{15}H_{22}N_2Cl_2O \cdot HCl$: Calculated: C, 50.73; H, 6.55; N, 7.92; Cl, 30.07. Found: C, 51.02; H, 6.58; N, 8.11; Cl, 30.54.

In the manner given in the prior examples other compounds of formula III can be prepared.

Representative compounds thus prepared comprise:
N-[(2-dimethylamino)ethyl]-3',4'-dibromoacrylanilide;
N-[(2-dimethylamino)ethyl]-3',4'-dibromocyclopropanecarboxanilide;
N-[(3-dimethylamino)propyl]-3',4'-dibromoacrylanilide;
N-[(3-dimethylamino)propyl]-3',4'-dichlorocyclopropanecarboxanilide;
N-[(3-dimethylamino-2-methyl)propyl]-3',4'-dichloropropionanilide;
N-[(3-dimethylamino-2-methyl)propyl]-3',4'-dichloroacrylanilide;
N-[(3-dimethylamino-2-methyl)propyl]-3',4'-dichlorocyclopropanecarboxanilide; and the like.

Treating these amino compounds of those of the examples with stoichiometrically calculated amounts of pharmacologically acceptable acids, one obtains the corresponding pharmaceutically acceptable acid addition salts of these amines. Such salts include the hydrochlorides, hydrobromides, hydroiodides, sulfates, phosphates, acetates, lactates, malates, maleates, succinates, tartrates, citrates, benzenesulfonates, methanesulfonates, sulfamates and the like.

EXAMPLE 26

One thousand two-piece hard gelatin capsules for oral use each containing 2.5 mg. of N-[3-(dimethylamino)propyl]-3',4'-dichloropropionanilide hydrochloride are prepared from the following types and amounts of material:

| | |
|---|---|
| N-[3-(dimethylamino)propyl]-3',4'-dichloropropionanilide hydrochloride | 2.5 gm. |
| Lactose | 150 gm. |
| Corn Starch | 25 gm. |
| Talc | 20 gm. |
| Magnesium Stearate | 2.0 gm. |

The materials are thoroughly mixed and then encapsulated in the usual manner. To alleviate depression in man, 1 to 2 capsules every 4 hours are administered.

Similarly, capsules containing 5, 20, 15, 20, 25 or 30 mg. of the active materials can be prepared by the same procedures.

EXAMPLE 27

One thousand tablets for oral use, each containing 25 mg. of N-[3-(dimethylamino)propyl]-3',4'-dichloropropionanilide hydrochloride are prepared from the following types and amounts of materials:

| | |
|---|---|
| N-[-3-(dimethylamino)propyl]-3',4'-dichloropropionanilide hydrochloride | 25 gm. |
| Lactose | 125 gm. |
| Corn Starch | 65 gm. |
| Magnesium Stearate | 2.5 gm. |
| Light Liquid Petrolatum | 3 gm. |

The ingredients are thoroughly mixed and slugged. The slugs are broken down by forcing through a number sixteen screen. The resulting granules are then compressed into tablets, each tablet containing 25 mg. of N-[3-(dimethylamino)propyl]-3',4'-dichloropropionanilide hydrochloride.

The foregoing tablets are useful for treatment of depression in adult humans by oral administration of 1 tablet, 1 to 3 times per day.

EXAMPLE 28
Oral Syrup

One thousand ml. of an aqueous suspension for oral use, containing in each 5 ml. dose, 10 mg. of N-[2-(dimethylamino)ethyl]-3',4'-dichloropropionanilide hydrochloride is prepared from the following types and amounts of ingredients:

| | |
|---|---|
| N-[2-(dimethylamino)ethyl]-3',4'-dichloropropionanilide hydrochloride | 2 gm. |
| Citric Acid | 2 gm. |
| Benzoic Acid | 1 gm. |
| Sucrose | 700 gm. |
| Tragacanth | 5 gm. |
| Lemon Oil | 2 ml. |
| Deionized water q.s. | 1000 ml. |

The citric acid, benzoic acid, sucrose, tragacanth, and lemon oil are dispersed in sufficient water to make 850 ml. of solution. N-[2-(dimethylamino)ethyl]-3',4'-dichloropropionanilide hydrochloride is stirred into the syrup until uniformly distributed. Sufficient water is added to make 1000 ml.

The composition so prepared is useful in the treatment of depression in adult humans at a dose of 1 teaspoonful 4 times a day.

EXAMPLE 29

Parenteral Solution p A sterile aqueous solution for intramuscular use, containing in 1 ml. 25 mg. of N-[3-(dimethylamino)propyl]-3',4'-dichloropropionanilide hydrochloride is prepared from the following types and amounts of materials:

| | |
|---|---|
| N-[3-(dimethylamino)propyl]-3',4'-dichloropropionanilide hydrochloride | 25 gm. |
| Lidocaine hydrochloride | 4 gm. |
| Methylparaben | 2.5 gm. |
| Propylparaben | 0.17 gm. |
| Water for injection q.s. | 1000 ml. |

The ingredients are dissolved in the water and the solution sterilized by filtration. The sterile solution is filled into vials and the vials sealed.

EXAMPLE 30
Suppository, Rectal

One thousand suppositories, each weighing 2.0 gm. and containing 5 mg. of N-[(2-dimethylamino-1-methyl)ethyl]-3',4'-dichloropropionanilide are prepared from the following types and amounts of ingredients:

| | |
|---|---|
| N-[(2-dimethylamino-1-methyl)ethyl]-3',4'-dichloropropionanilide | 5 gm. |
| Propylene Glycol | 162.5 gm. |
| Polyethylene Glycol 4000 q.s. | 2000 gm. |

The N-[(2-dimethylamino-1-methyl)ethyl]-3',4'-dichloropropionanilide hydrochloride is added to the propylene glycol and the mixture milled until the powders are finely divided and uniformly dispersed. The polyethylene glycol 4000 is melted and the propylene glycol dispersion added slowly with stirring. The suspension is poured into unchilled molds at 40° C. The composition is allowed to cool and solidify and then removed from the mold and each suppository foil wrapped.

The suppositories are useful in the alleviation of depression by the insertion rectally of 1 suppository every four hours.

EXAMPLE 31

Compositions are similarly prepared following the procedure of the preceding Examples 26 through 30 substituting as active ingredient an equimolar amount each of N-[(3-dimethylamino-2-methyl)ethyl]-3',4'-dichloropropionanilide;

N-[(3-dimethylamino-2-methyl]propyl]-3',4'-dichloropropionanilide;

N-[3-dimethylamino-2-methyl)propyl]-3',4'-dibromocyclopropanecarboxanilide;

N-[(3-dimethylamino-2-methyl)propyl]-3',4'-dibromoacrylanilide;

N-[(3-dimethylamino-1-methyl)propyl]-3',4'-dibromoacrylanilide;

N-[(3-dimethylamino-1-methyl)propyl]-3',4'-dibromocyclopropanecarboxanilide;

N-[2-(dimethylamino)ethyl]-3',4'-dibromopropionanilide;

N-[3-(dimethylamino)propyl]-3',4'-dibromopropionanilide;

N-[(2-dimethylamino-1-methyl)ethyl]-3',4'-dichloroacrylanilide;

N-[(2-methylamino-2-methyl)]ethyl]-3',4'-dichloroacrylanilide;

as well as hydrochlorides, hydrobromides, sulfates, tartrates, lactates, citrates, methanesulfonates, maleate, malates, sulfamates, or the like, acid addition salts of the bases given above.

We claim:

1. A compound of the formula

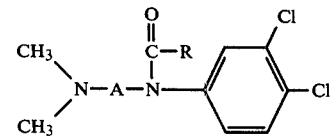

wherein A is alkylene of two to 3 carbon atoms, inclusive;

wherein R is ethyl, cyclopropyl or vinyl, or the pharmacologically acceptable acid addition salts thereof.

2. A compound of the formula

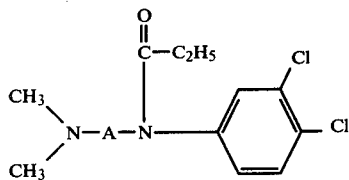

wherein A is alkylene of two to 3 carbon atoms, inclusive, or the pharmacologically acceptable acid addition salts thereof.

3. A compound of the formula

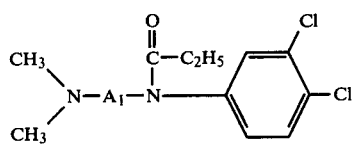

wherein $A_1$ is ethylene or trimethylene or the pharmacologically acceptable acid addition salts thereof.

4. A compound according to claim 3, wherein $A_1$ is ethylene, N-[2-(dimethylamino)ethyl]-3',4'-dichloropropionanilide.

5. The hydrochloride of the compound of claim 4.

6. A compound according to claim 3, wherein $A_1$ is trimethylene, N-[3-(dimethylamino)propyl]-3',4'-dichloropropionanilide.

7. The hydrochloride of the compound of claim 6.

8. A compound according to claim 2, wherein A is

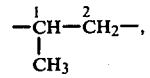

N-[(2-dimethylamino-1-methyl)ethyl]-3',4'-dichloropropionanilide.

9. The hydrochloride of the compound of claim 8.

10. A compound according to claim 2, wherein A is

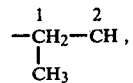

N-[(2-dimethylamino-2-methyl)ethyl]-3',4'-dichloropropionanilide.

* * * * *

UNITED STATES PATENT OFFICE
CERTIFICATE OF CORRECTION   Page 1 of 2

Patent No.  4,180,522                           Dated  25 December 1979

Inventor(s)  Michael P. Kane, et al.

It is certified that error appears in the above-identified patent and that said Letters Patent are hereby corrected as shown below:

Abstract, second occurrence of formula should be deleted and replaced by

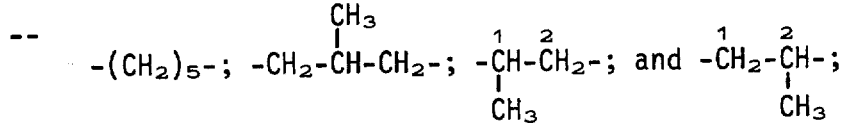

Column 1, lines 28-54, should read

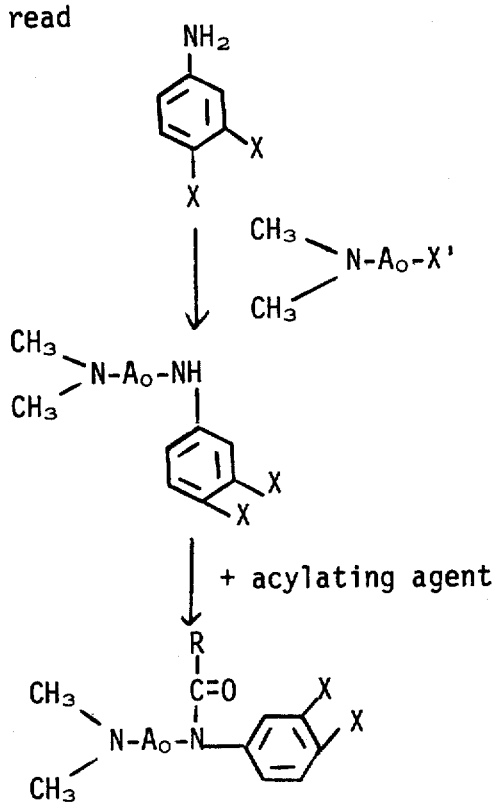

UNITED STATES PATENT OFFICE
CERTIFICATE OF CORRECTION

Patent No. 4,180,522          Dated 25 December 1979

Inventor(s) Michael P. Kane, et al

It is certified that error appears in the above-identified patent and that said Letters Patent are hereby corrected as shown below:

Column 4, line 55, "anti-depressand" should read -- anti-depressant --;

Column 6, line 66, "$C_{10}H_{14}Cl_2N_2 \cdot 2HCl \cdot {}_2CH_3OH$:" should read -- $C_{20}H_{14}Cl_2N_2 \cdot 2HCl \cdot \frac{1}{2}CH_3OH$: --

Column 15, line 68, "tetrahydrofuarn" should read -- tetrahydrofuran --;
Column 16, line 66, "5, 20, 15, 20, 25 or 30" should read
            -- 5, 10, 15, 20, 25 or 30 --;
Column 17, line 53, "Parenteral Solution p A sterile" should read
            -- Parenteral Solution  A sterile --;
Column 20, lines 24-25 (Claim 10)

Signed and Sealed this

Twenty-third Day of December 1980

[SEAL]

Attest:

SIDNEY A. DIAMOND

Attesting Officer            Commissioner of Patents and Trademarks